United States Patent
Liu

(10) Patent No.: US 6,534,319 B1
(45) Date of Patent: Mar. 18, 2003

(54) CHEMICAL SENSOR AND COATING FOR SAME

(75) Inventor: Guojun Liu, Ames, IA (US)

(73) Assignees: Fisher Controls International, Inc., Austin, TX (US); Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/413,676

(22) Filed: Oct. 6, 1999

(51) Int. Cl.$^7$ .................................................. G01N 27/416
(52) U.S. Cl. ........................ 436/151; 436/124; 436/806; 422/82.01; 422/82.03
(58) Field of Search .................................. 436/151, 806, 436/124; 422/82.01, 82.03

(56) References Cited

U.S. PATENT DOCUMENTS

| | | | |
|---|---|---|---|
| 4,530,569 A | 7/1985 | Squire | 385/145 |
| 4,754,009 A | 6/1988 | Squire | 526/247 |
| 4,948,851 A | 8/1990 | Squire | 526/247 |
| 4,973,142 A | 11/1990 | Squire | 359/642 |
| 4,975,505 A | 12/1990 | Squire | 526/247 |
| 4,977,008 A | 12/1990 | Squire | 428/35.7 |
| 4,977,025 A | 12/1990 | Squire | 428/421 |
| 4,977,026 A | 12/1990 | Squire | 428/422 |
| 4,977,297 A | 12/1990 | Squire | 174/258 |
| 4,982,056 A | 1/1991 | Squire | 174/258 |
| 4,985,308 A | 1/1991 | Squire | 428/422 |
| 4,999,248 A | 3/1991 | Squire | 428/422 |
| 5,000,547 A | 3/1991 | Squire | 359/642 |
| 5,006,382 A | 4/1991 | Squire | 428/35.7 |
| 5,076,659 A | 12/1991 | Bekiarian et al. | 385/143 |
| 5,264,368 A | * 11/1993 | Clarke et al. | 436/3 |
| 5,530,264 A | * 6/1996 | Kataoka et al. | 257/40 |
| 5,546,802 A | * 8/1996 | Yoshimura et al. | 73/335.05 |
| 5,637,198 A | * 6/1997 | Breault | 204/165 |
| 5,756,879 A | * 5/1998 | Yamagishi et al. | 73/28.01 |
| 6,237,397 B1 | * 5/2001 | Shinar et al. | 73/24.06 |

OTHER PUBLICATIONS

Analytical Chemistry. "High–Sensitivity Gas Sensors Based on Gas Permeable Liquid Core Waveguides and Long–Path Absorbance Detection". Dasgupta et al. vol. 70, No. 22. pp. 4661–4669. Oct. 1998.*

Jay W. Grate, Stephen J. Martin, and Richard M. White, Acoustic Wave Microsensors Part II, Analytical Chemistry, vol. 65, No. 22, Nov. 15, 1993, pp. 987–996.

Daniel A. Buttry and Michael D. Ward, Measurement of Interfacial Process at Electrode Surfaces with the Electrochemical Quartz Crystal Microbalance, Chemical Reviews 1992, 92, pp. 1355–1379. Jun. 1992.

Warren H. Buck and Paul R. Reanick, TEFLON® AF, May 17, 1993.

(List continued on next page.)

*Primary Examiner*—Jill Warden
*Assistant Examiner*—Latoya Cross
(74) *Attorney, Agent, or Firm*—Marshall, Gerstein & Borun

(57) ABSTRACT

A chemical sensor utilizing a substrate and a fluoropolymer coating is disclosed. Transducers may be connected to the substrate to generate an alternating potential across the substrate, which in turn causes the substrate to resonate due to the converse piezoelectric effect. The polymer coating absorbs the analyte, thus changing the mass of the sensor, and accordingly changing its resonant frequency. The transducers detect this change in resonant frequency to indicate to the operator that the analyte is present. The use of amorphous copolymers of 2,2-bistrifluoromethyl-4,5-difluoro-1,3-dioxole (PDD), and tetrafluoroethylene (TFE) allows for improved sensitivity and responsiveness while also allowing for robust characteristics enabling the sensor to be used in a variety of environmental conditions.

8 Claims, 2 Drawing Sheets

OTHER PUBLICATIONS

William H. King, Jr., Piezoelectric Sorption Detector, Analytical Chemistry, vol. 36, No. 9, Aug. 1964, pp. 1735–1739.

Stephen J. Martin and Stephen D. Senturla, Dynamics and Response of Polymer–Coated Surface Acoustic Wave Devices: Effect of Viscoelastic Properties and Film Resonance, Analytical Chemistry, vol. 66, No. 14, Jul. 15, 1994, pp. 2201–2219.

Jay W. Gate and Samuel J. Patrash, Method for Estimating Polymer–Coated Acoustic Wave Vapor Sensor Responses, Jul. 1, 1995, Analytical Chemistry, vol. 67, No. 13, Jul. 1, 1995, pp. 2162–2169.

Edward T. Zellers and Mingwei Han, Effects of Temperature and Humidity on the Performance of Polymer–Coated Surface Acoustic Wave Vapor Sensor Arrays, Analytical Chemistry, vol. 68, No. 14, Jul. 15, 1996, pp. 2409–2418.

K. K. Kanazawa, A General Solution for the Change in Mechanical Resonance of a Quartz Oscillator Due to Viscoelastic Overlayers, Apr. 30, 1986, pp. 1–22.

Ralph Lucklum, Carsten Behling, Richard W. Cernosek, and Stephen J. Martin, Determination of Complex Shear Modulus with Thickness Shear Mode Resonators, J. Phys. D: Appl. Phys. 30 1997, pp. 346–356.

* cited by examiner

CHEMICAL SENSOR AND COATING FOR SAME

FIELD OF THE INVENTION

The present invention generally relates to systems for monitoring environmental contaminants and, more particularly, to systems for monitoring fugitive emissions from process equipment.

BACKGROUND OF THE INVENTION

Industrial plants which handle volatile organic compounds (VOCs) typically experience unwanted emissions of such compounds into the atmosphere from point sources, such as smoke stacks, and non-point sources, such as valves, pumps, and fittings installed in pipes and vessels containing the VOCs. Such VOCs include, but are not limited to, aromatics (e.g., benzene, toluene, ethylbenzene, and xylenes), halogenated hydrocarbons (e.g., carbon tetrachloride, 1,1,1-trichloroethane, and trichloroethylene), ketones (e.g., acetone, and methyl ethyl ketone), alcohols (e.g., methanol, ethanol, and propanol), ethers (e.g., dimethyl ether and methyl t-butyl ether), and aliphatic hydrocarbons (e.g., natural gas and gasoline).

Emissions from non-point sources, referred to as fugitive emissions, typically occur due to the leakage of the VOCs from joints and seals. Fugitive emissions from control valves may occur as the result of leakage through the packing between the valve stem and the body or bonnet of the valve. Valves employed in demanding service conditions involving frequent movement of the valve stem and large temperature fluctuations typically suffer accelerated deterioration of the valve stem packing, which results in greater fugitive emissions than valves employed in less demanding service.

While improvements in valve stem packing materials and designs have reduced fugitive emissions and lengthened the life of valve packing, the monitoring of fugitive emissions has become important as a means to identify and reduce fugitive emissions, and to comply with the more stringent regulation of emissions. For example, the Environmental Protection Agency (EPA) has promulgated regulations for specifying the maximum permitted emission of certain hazardous air pollutants from control valves, and requires periodic surveys of emissions from control valves.

Current methods of monitoring fugitive emissions involve manual procedures using a portable organic vapor analyzer. This manual method is time consuming and expensive to perform, and can also yield inaccurate results due to ineffective collection of the fugitive emissions from the equipment being monitored. If measurements are made on a valve exposed to wind, emissions from the valve may be dissipated before the analyzer can properly measure the concentration of the emissions. Also, if the analyzer is not carefully moved around the valve to capture all the emissions from the valve, an inaccurate measurement will result. Manual measurement methods also require plant personnel to dedicate a significant amount of time to making the measurements, thereby distracting plant personnel from other duties.

Automated monitoring and detection of fugitive emissions can yield significant advantages over existing manual methods. The EPA regulations require surveys of fugitive emissions at periodic intervals. The length of the survey interval may be monthly, quarterly, semi-annually, or annually, with the required surveys becoming less frequent if the facility operator can document a sufficiently low percentage of control valves exhibiting excessive leakage. Thus, achieving a low percentage of leaking valves reduces the number of surveys required per year. In a large industrial facility, where the total number of survey points can range from 50,000 to 200,000, a reduced number of surveys can result in large cost savings. By installing automated fugitive emission-sensing systems on valves subject to the most demanding service conditions, and thus, most likely to develop leaks, compliance with the EPA regulations can be more readily achieved for the entire facility.

However, employing chemical sensors in an industrial environment requires designing sensors that perform satisfactorily in the presence of high relative humidity across a broad temperature range. The sensors must be able to discriminate between the emissions of interest and other environmental contaminants, while retaining sufficient sensitivity to detect low concentrations of the fugitive emissions. A provision also must be made to enable periodic calibration of the chemical sensors. The output signals from the fugitive emission sensing system must be suitable for input into plant monitoring and control systems typically found in process plants. This permits simple and inexpensive integration of the sensing system into existing plant process control systems.

The fugitive emission sensing system must be inexpensive to manufacture, and use a power source that is readily available in a typical process plant in order to keep installation costs to a minimum. The system must be suitable for use in hazardous areas subject to risk of explosion, requiring electrical equipment to be intrinsically safe or of an explosion-proof design. It also must be able to operate in harsh environments, including areas subject to spray washing, high humidity, high and low temperatures, and vibration. The system also must be simple and reliable, in order to keep maintenance costs to a minimum.

In certain applications, the sensors used to detect fugitive emissions are provided in the form of piezoelectric-based sensors having high sensitivities to surface mass changes, such that when an alternating potential is applied across the sensors, changes in resulting wave characteristics in the sensors, specifically the resonant frequency, indicate the presence of the analyte. More specifically, the sensors typically include a quartz crystal substrate with an outer layer made of material selected to most effectively absorb the analyte. Such outer coatings are selected to increase sensitivity, while reducing acoustic wave damping effects. In addition, such materials should be environmentally robust to accommodate the aforementioned wide temperature ranges, humidity ranges, and high levels of dust particles and other contaminants.

SUMMARY OF THE INVENTION

In accordance with one aspect of the present invention, a sensor is provided which may include a substrate, at least two electrodes connected to the substrate, and a layer of fluoropolymer positioned over the substrate and at least one of the electrodes.

In accordance with another aspect of the present invention, the fluoropolymer is a copolymer of 2-2-bistrifluoromethyl 1-4,5-difluoro-1,3-dioxole. The copolymer may comprise tetrafluoroethylene.

In accordance with another aspect of the invention, a method of detecting volatile organic compounds using a sensor is provided. The sensor comprises a substrate, at least two electrodes connected to the substrate, and a coating positioned over the substrate and at least one of the electrodes. The coating is a fluoropolymer.

These and other aspects and features of the present invention will become more apparent from the following detailed description when taken in conjunction with the accompanying drawings.

Figure 1:
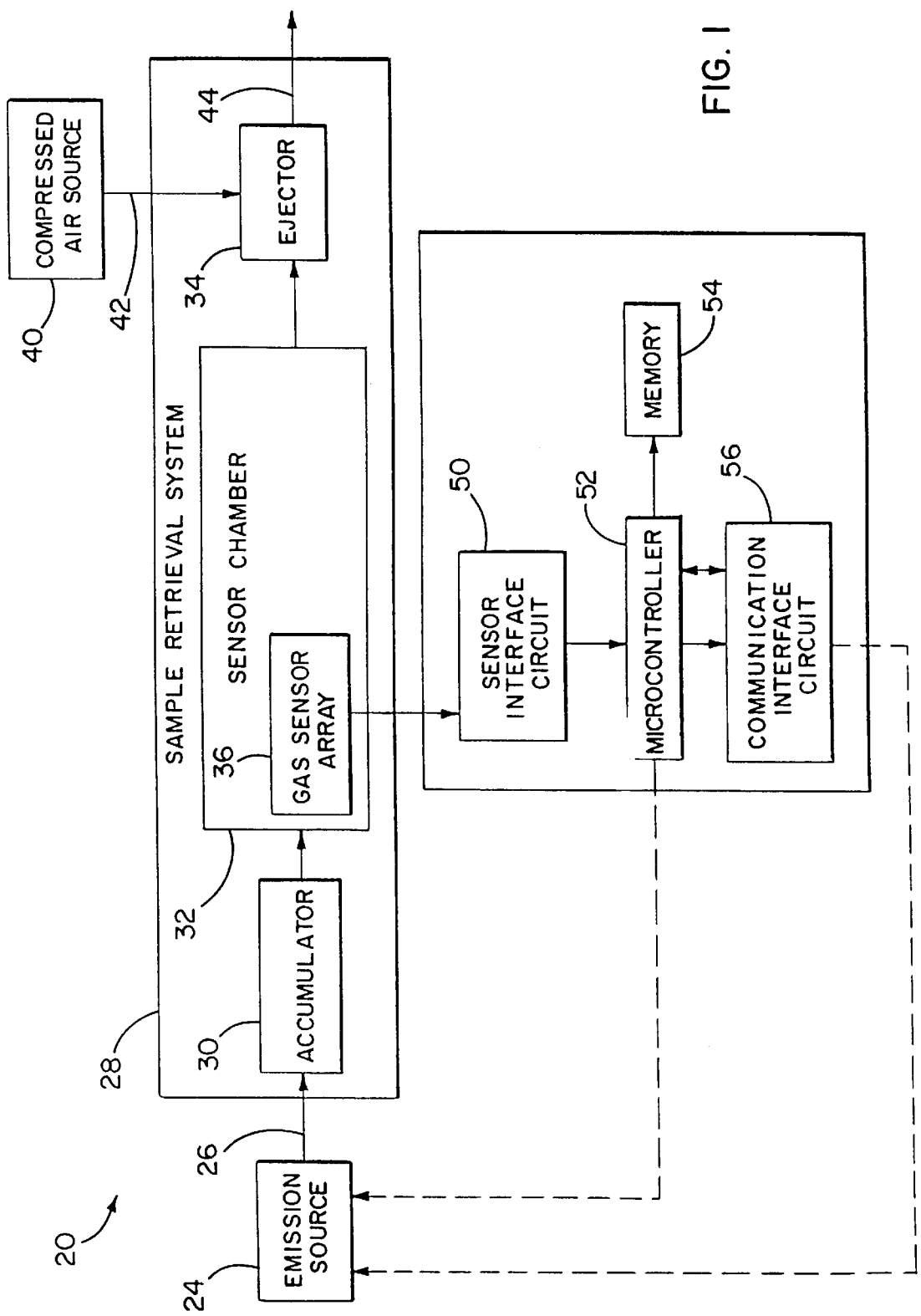
FIG. 1 is a block diagram of a fugitive emissions sensing system employing the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but on the contrary, the intention is to cover all modifications, alternative constructions, and equivalents, falling within the spirit and scope of the invention as defined by the appended claims.

DETAILED DESCRIPTION OF THE INVENTION

Referring now to the drawings, and with specific reference to FIG. 1, a fugitive emissions sensing system utilizing the present invention is generally depicted by reference numeral 20. However, it is to be understood that the present invention is primarily directed to a chemical sensor 22 (FIG. 2) which can be employed in a variety of applications, including applications separate from the fugitive emissions sensing system 20.

By way of overview, FIG. 1 is a block diagram of an illustrative fugitive emissions sensing system 20 employing the chemical sensor 22. An emission source 24 is shown, from which a sample stream 26 is drawn into sample retrieval system 28. The sample retrieval system 28 includes an accumulator 30, a sensor chamber 32, and an ejector 34. A chemical sensor array 36 is located within the sensor chamber 32. The sample stream 26 is drawn from the accumulator 30 into the sensor chamber 32, exposing the chemical sensor array 36 to the sample stream 26. The chemical sensor array 36 contains one or more of the chemical sensors 22. The sample stream 26 then passes into the ejector 34. A compressed air source 40 provides compressed air 42 to the ejector 34, creating a pressure drop within the ejector 34 which draws a sample stream 26 through the sensor chamber 32 and into the ejector 34. The compressed air 42 and sample stream 26 are mixed within the ejector 34 and exhausted to atmosphere as a mixture 44.

The gas sensor array 36 is connected to a sensor interface circuit 50, which processes the signals from the sensor array 36 and provides the process signals to a microcontroller 52. The microcontroller 52 stores the data from the sensors 22 in a memory 54, and uses the sensor data received from the fugitive emissions sensing system 20 to initiate control actions to reduce or eliminate the emissions. For example, the microcontroller 52 could close a valve upstream from the emissions source 24 to stop the flow of fluid through the emissions source 24 in order to stop emissions caused by the leakage of the fluid. Alternatively, the microcontroller 52 could alter operating conditions of the emissions source 24 itself to reduce or eliminate the fugitive emissions. The microcontroller 52 may use a communication interface circuit 56 to provide control signals to the upstream valve, the emission source 24, or any other equivalent that may be used to reduce or eliminate the emissions.

It can therefore be seen that the fugitive emissions sensing system 20 may be used to detect the presence of, or measure the concentration of, various types of fluids emitted from the emissions source 24. The system may be used to detect hazardous, toxic or polluting substances emitted from the source, or to detect leakage of non-hazardous substances, the loss of which may be a cause of concern. The fugitive emission sensing system 20 may be used to detect emissions from any kind of source, particularly industrial process equipment from which hazardous substances may leak. Examples include control valves, block valves, pumps installed on lines carrying hazardous gases, agitators, screw conveyors, or other equipment installed on process vessels containing hazardous fluids, heat exchanges, reactors, etc. When emissions are detected by the fugitive emissions sensing system 20, this data may be used by the fugitive emissions sensing system 20 to control the process in such a way as to reduce or eliminate the emissions.

As indicated above, the chemical sensor array 36 may include one or more chemical sensors 22 responsive to a particular analyte or fugitive emission being monitored. In the embodiment depicted in FIG. 2, the chemical sensor 22 is a quartz crystal microbalance (QCM) sensor, but can be another type of piezoelectric acoustic wave devices, including surface acoustic wave (SAW) devices, acoustic plate mode (APM) devices, and flexural plate wave (FPW) devices. Alternatively, fiber optic sensors and electrochemical sensors may be used.

Figure 2:
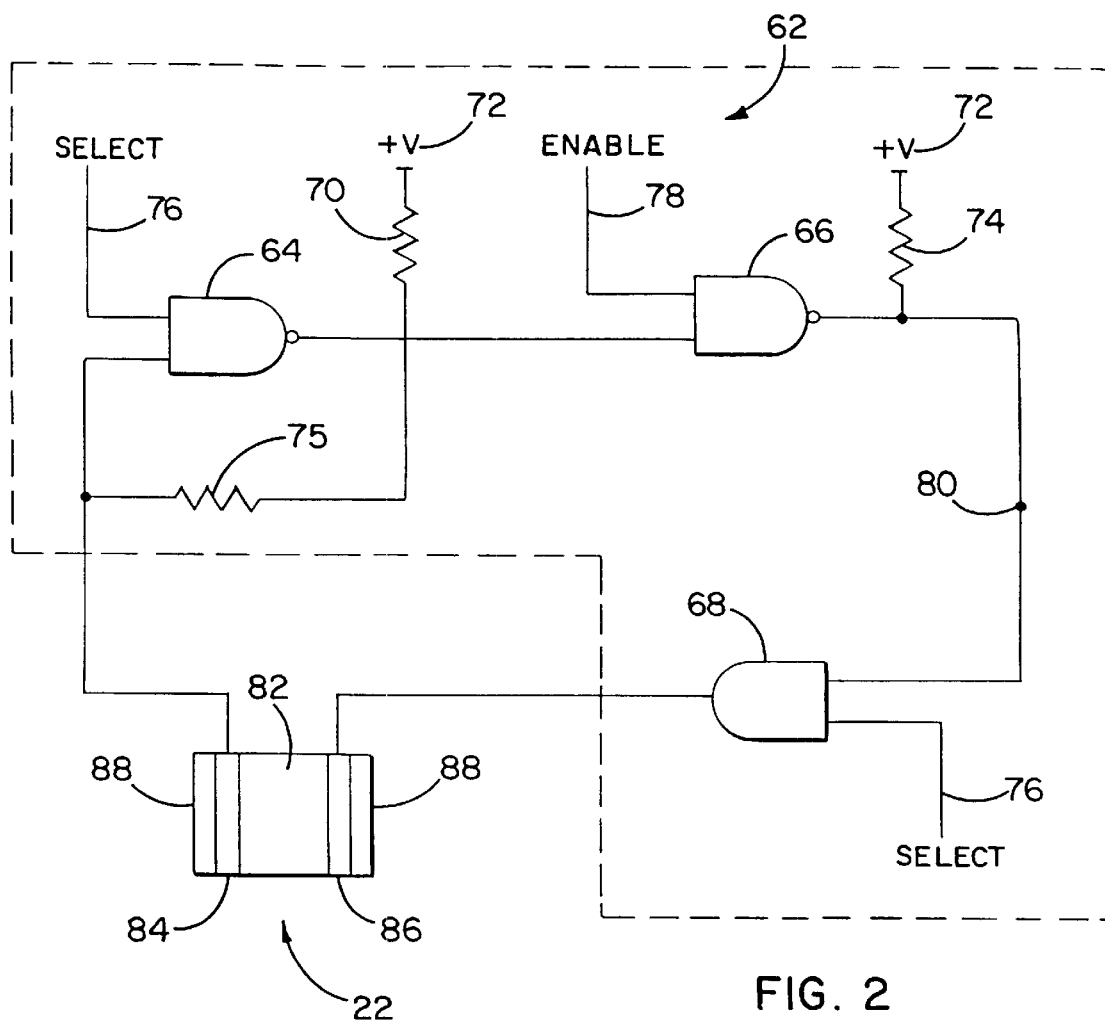
FIG. 2 is a schematic diagram of a chemical sensor circuit including one embodiment of the chemical sensor of the present invention.

As shown in FIG. 2, the chemical sensor 22 may be connected to an oscillator circuit 62 for monitoring emissions. In an alternative embodiment, the chemical sensor 22 could be connected to a network analyzer. More specifically, the oscillator circuit 62 may include NAND gates 64 and 66, and an AND gate 68, connected in series. A resistor 70 may be connected between the output of the NAND gate 66 and the circuit power supply voltage 72, and a resistor 74 may be connected between the output of NAND gate 66 and circuit power supply voltage 72. A resistor 75 may be connected across the NAND gate 64, connecting a first input to the output. A select signal 76 may be connected to the second input of the NAND gate 64, and the same select signals may also be connected to an input of the AND gate 68. An enable signal 78 may be connected to an input of the NAND gate 66. When the select signal 76 and the enable signal 78 are both high, the NAND gates 64 and 66 act as high-gain inverting amplifiers and cause an oscillator 80 to oscillate between high and low voltage, producing an oscillating square wave output. The oscillating voltage from the oscillator output 80 may be transferred through the AND gate 68 and applied across the chemical sensor 22 causing the chemical sensor 22 to physically resonate.

In order to appreciate the significance of this resonance, it is first important to understand that the chemical sensor 22 utilizes the converse piezoelectric effect. By way of background, the piezoelectric effect holds that a mechanical stress applied to the surfaces of various crystals, including quartz, affords a corresponding electrical potential across the crystal having a magnitude proportional to the applied stress. The electrical charge generated in the quartz crystal under stress is due to the shift of dipoles resulting from the displacement of atoms in the crystalline material. The converse piezoelectric effect holds that application of a voltage across certain crystals, including quartz crystals, results in a corresponding mechanical strain in the crystal. In quartz, this strain or deformation is elastic. It follows that an alternating potential across the crystal causes a vibrational motion in the quartz crystal, i.e., the aforementioned resonance. The chemical sensor 22 therefore includes a crystal substrate 82 which interacts with the oscillating circuit 62, and in turn causes the oscillator circuit 62 to oscillate at the resonant frequency of the chemical sensor 22. Thus, the frequency of the oscillator output 80 will vary as the resonant frequency of the chemical sensor 22 varies.

The resonant frequency of the chemical sensor 22 can vary based on a number parameters, including the mass, size, shape, and cut of the quartz crystal substrate 82. Quartz crystal exhibits a natural resonant frequency that is a function of the mass and structure of the crystal. The precise size, type of cut, and thickness of the quartz crystal substrate 82 are selected to result in a particular resonant frequency. For example, an AT-cut crystal with a nominal resonant frequency of 8–30 megahertz is suitable for gas sensor applications. Suitable quartz crystal substrates may be obtained from Standard Crystal Corporation of California. Other types of suitable materials to serve as the substrate include lithium niobate ($LiNbO_3$), which is particularly suited for a surface acoustic wave (SAW) based-sensor; and aluminum nitride (AlN), which is particularly suited for a thin film resonator based-sensor.

In order to apply the alternating potential across the substrate 82, first and second electrodes 84 and 86 are connected to the crystal substrate 82 and may be constructed of gold-on-chromium, although other suitable corrosion-resistant conductors may be used, possibly including aluminum, palladium, gold, chromium, and graphite. The electrodes 84 and 86 may serve as both the conductors for generating the alternating current across the crystal substrate 82, and as transducers for sensing parameters related to changes in resonant frequencies resulting in the crystal substrate 82.

As indicated above, the resonant frequency of the chemical sensor 22 is a function of the total mass of the device. Therefore, the mass of any coating provided around the crystal substrate 82 also affects the total mass of the device, and thereby affects the resonant frequency of the chemical sensor 22. The coatings provided about the crystal substrate 82 are selected to absorb molecules of the analyte. When analyte molecules are absorbed by the coating, the mass of the coating is slightly increased, which in turn increases the mass of the entire sensor 22, and thus changes the resonant frequency of the sensor 22. The resonant frequency of the chemical sensor 22 is also a function of the viscoelastic properties of the coatings and mechanical stresses caused by temperature effects in the sensor mounting structure. However, these effects are either negligible or can be compensated for. Thus, a very sensitive chemical detector may be constructed by selecting a coating that has a chemical affinity with the particular analyte of interest. The quantity of molecules absorbed and deposited, and the resulting change in the operating frequency of the oscillator circuit 62, is a function of the concentration of the analyte being measured in the environment surrounding the chemical sensor 22. The frequency changes linearly with changes in analyte concentration, within certain limits.

Thus, a change in the concentration of the analyte may be measured by measuring the change in the frequency of the oscillator output 80. The chemical sensor 22 may be calibrated by exposing the chemical sensor 22 to known concentrations of the analyte and recording the resulting frequency of the oscillator output 80. The chemical sensor 22 may then be used to measure the absolute concentration of the analyte by comparing the measured frequency to the aforementioned recorded values.

The particular coating chosen for the crystal substrate 82 should preferably readily absorb the molecules of the analyte, to provide fast response times and a high degree of sensitivity to the analyte over a broad temperature range, but do so without damping the generated waves. The present invention provides such a coating in the form of a fluoropolymer coating 88. The fluoropolymer may be a copolymer comprising perfluoro-2,2-dimethyl-1,3-dioxole. The comonomer typically is fluorinated. Useful fluoropolymers are disclosed in U.S. Pat. Nos. 4,754,009 and 5,000,547, the disclosures of which are expressly incorporated herein by reference. An especially preferred fluoropolymer coating 88 is commercially available from Dupont Fluoroproducts, Wilmington, Del., under the tradename TEFLON® AF. TEFLON® AF is a copolymer of 2,2-bistrifluoromethyl-4, 5-difluoro-1,3-dioxole (PDD) and tetrafluoroethylene (TFE).

A preferred fluoropolymer for coating 88 has the following combination of properties:

1. High glass transition temperature of at least 160° C.;
2. High moduli, especially at elevated temperatures;
3. High strength, especially at elevated temperatures;
4. Low creep under compressive load;
5. Melt fabricability at moderate temperatures;
6. Fabricability into films and coatings by solvent casting;
7. Low temperature sprayability;
8. Low refractive index;
9. Excellent dielectric properties; and
10. Excellent chemical resistance.

Unexpectedly, the high glass transition temperature fluoropolymer used in the present invention overcomes the undesirable properties inherent in high glass transition temperature polymers. High glass transition temperature polymers typically are unsuitable for sensor applications because of slow and hysteresis responses to analytes. The high glass transition fluoropolymer, however, also has acoustic wave properties superior to conventional low glass transition temperature polymers, like poly(isobutylene) and poly(diphenoxy phosphazene).

Accordingly, the fluoropolymer coating improves upon the performance of low glass transition temperature polymers, and overcomes the disadvantages of high glass transition temperature polymers. For example, the fluoropolymer coating 88 has a high glass transition temperature, and does not damp sensor transducers to the same degree as low glass transition polymers.

A relatively thick film of the fluoropolymer coating 88, e.g. a coating of about 1 to about 10 microns, can be deposited on the crystal substrate 82. A preferred coating thickness is about 2 to about 8 microns, and to achieve the full advantage of the present invention, the coating thickness is about 3 to about 6 microns. Persons skilled in the art are capable of determining the optimum coating thickness from consideration of use temperatures, desired response time, and expected analyte concentrations. A relatively thick coating increases the sensitivity of the chemical sensor 22 because the sensitivity is generally proportional to the thickness of the coating 88. Moreover, given the aforementioned benefits, use of such a fluorinated copolymer as the coating 88 allows the sensor 22 to be used in a wide range of temperatures without compromising performance.

Unlike other high glass transition polymer films, the fluoropolymer coating 88 exhibits fast and reversible responses to volatile organic compounds of low molecular weight. In addition, the fluoropolymer coating 88 is chemically inert and less susceptible to environmental aging, e.g., attacks from ozone and oxidizing gases. This improves the stability and lifetime of the chemical sensor 22. The fluoropolymer coating 88 is also hydrophobic, such that interference due to water vapor and polar volatile organic chemicals has a low impact on performance. Since it has low-surface energy, the fluoropolymer coating 88 has a low tendency to collect foreign objects, such as dust particles, and thus needs a low degree of care. The fluoropolymer coating 88 is also soluble in a commercial solvent at ambient temperature, thus facilitating application of the coating 88 to the crystal substrate 82 using conventional methods. Suitable solvents for such use include solvents having a mixture of fluorinated hydrocarbons, such as the solvent marketed under the tradename FC-75 FLUORINERT® by 3M Corporation, St. Paul, Minn.

In accordance with the present invention, the fluoropolymer coating may be applied to the crystal substrate and electrodes using the following procedure. The crystal substrate and electrodes are first cleaned using acetone and methanol. The TEFLON AF® is then dissolved in a fluorinated hydrocarbon solvent to produce a solution having a concentration of 1–6% TEFLON AF®, by weight. The concentration of TEFLON AF® in the solution is related to the desired coating thickness. The more concentrated the solution, the thicker the resulting coating will be. Approximately 7–10 drops of the solution is then applied to the substrate and electrodes to completely cover one side of the sensor. The coated substrate is then placed on a spin coater, a machine adapted to rotate at variable speed, with the preferred speed range being 500–6000 RPM, for a duration of approximately two minutes. The selected spin rate depends on the targeted coating thickness, with higher spin rates being selected for thinner coatings. After spin coating, the sensor is air dried for approximately one minute, with the aforementioned steps then being repeated for each side of the sensor. The sensor is then cured at a temperature of 100° C. for approximately two hours. Alternatively, if the coating is being applied to surface acoustic wave sensors or thin film resonator sensors, spray-coating and dip-coating techniques may be employed, respectively.

From the foregoing, it can therefore be seen that the present invention provides an improved chemical sensor and coating for a chemical sensor.

What is claimed is:

1. A volatile organic compound acoustic wave-based chemical sensor, comprising:
   a substrate;
   at least two electrodes connected to the substrate; and
   a sensing layer to sorb and retain the volatile organic compound wherein the sensing layer is positioned over the substrate and at least one of the electrodes, the sensing layer consisting only of an amorphous flouropolymer coating.

2. The chemical sensor of claim 1, wherein the amorphous fluoropolymer has a glass transition temperature of at least 160° Celsius.

3. The chemical sensor of claim 1, wherein the amorphous fluoropolymer has a thickness of about 1 micron to about 10 microns.

4. The chemical sensor of claim 1 wherein the substrate is selected from the group consisting of quartz crystal, lithium niobate, and aluminum nitrite.

5. A method of detecting volatile organic compounds comprising the steps of:
   collecting an analyte;
   exposing at least one acoustic wave-based chemical sensor to the analyte, the chemical sensor comprising a substrate, at least two electrodes connected to the substrate, and a coating to sorb the volatile organic compound, the coating positioned over at least one electrode wherein the coating consists only of amorphous flouropolymer coating;
   accumulating data from the chemical sensor; and
   computing the volumetric concentration of the analyte from the data.

6. The method of claim 5, wherein the amorphous fluoropolymer has a glass transition temperature of at least 160° Celsius.

7. The method of claim 5, wherein the amorphous fluoropolymer has a thickness of about 1 micron to about 10 microns.

8. The method of claim 5, wherein the substrate is selected from a group consisting of quartz crystal, lithium niobate, and aluminum nitrite.

* * * * *